(12) United States Patent
Mori

(10) Patent No.: US 9,510,958 B2
(45) Date of Patent: Dec. 6, 2016

(54) ELECTRICALLY POWERED ARTIFICIAL HAND

(71) Applicant: Institute of National Colleges of Technology, Japan, Tokyo (JP)

(72) Inventor: Takahiko Mori, Gifu (JP)

(73) Assignee: Insitute of National Colleges of Technology, Tokyo (JP)

( * ) Notice: Subject to any disclaimer, the term of this patent is extended or adjusted under 35 U.S.C. 154(b) by 0 days.

(21) Appl. No.: 14/405,803

(22) PCT Filed: May 9, 2013

(86) PCT No.: PCT/JP2013/063004
§ 371 (c)(1),
(2) Date: Dec. 5, 2014

(87) PCT Pub. No.: WO2013/190928
PCT Pub. Date: Dec. 27, 2013

(65) Prior Publication Data
US 2015/0182355 A1      Jul. 2, 2015

(30) Foreign Application Priority Data

Jun. 22, 2012   (JP) ................................ 2012-140417

(51) Int. Cl.
*A61F 2/76*      (2006.01)
*A61F 2/58*      (2006.01)
(Continued)

(52) U.S. Cl.
CPC ................. *A61F 2/72* (2013.01); *A61F 2/583* (2013.01); *A61F 2/588* (2013.01);
(Continued)

(58) Field of Classification Search
CPC ............ A61F 2/54; A61F 2/583; A61F 2/588; A61F 2/72; A61F 2002/7625; A61F 2002/7635; A61F 2002/6872; A61H 2230/60; A61H 2230/605; A61B 2562/0261; A61B 2562/0266
See application file for complete search history.

(56) References Cited

U.S. PATENT DOCUMENTS 3,866,246 A    2/1975  Seamone et al.
4,074,367 A    2/1978  Loveless
(Continued)

FOREIGN PATENT DOCUMENTS

GB          2302949          2/1997

OTHER PUBLICATIONS

Lobo-Prat, Joan. Non-invasive control interfaces for intention detection in active movement-assistive devices. Journal of NeuroEngineering and Rehabilitation 2014, 11:168.*
(Continued)

*Primary Examiner* — Thomas J Sweet
*Assistant Examiner* — Christie Bahena
(74) *Attorney, Agent, or Firm* — Trego, Hines & Ladenheim, PLLC

(57) ABSTRACT

The invention addresses the problem of providing an electrically powered artificial hand that can be constructed with a simple configuration, the operation of which is easy to master and the control of which is highly reproducible. The electrically powered artificial hand (1) is provided with: a shape-detecting sensor (2) for detecting the shape of the forearm of an upper limb amputee; a hand section (6) having a pair of arms (7a, 7b) that are capable of opening and closing movements; and a main control unit body (8) having a sensor signal-receiving circuit for receiving the sensor signal output from the shape-detecting sensor (2) according to the shape of the forearm, and a control signal-generating and -sending circuit for generating a control signal on the
(Continued)

basis of the sensor signal and sending the control signal to the hand section (6) to control the opening and closing movements of the arms (7a, 7b). The control signal comprises a control direction for controlling the direction of the movement of arms (7a, 7b), the direction being determined on the basis of the direction of the change in shape from a previously prescribed initial shape of the forearm, and a control magnitude for controlling the distance of movement of the arms (7a, 7b), the magnitude being determined on the basis of the magnitude of the change in shape from the initial shape.

6 Claims, 3 Drawing Sheets

(51) Int. Cl.
A61F 2/72 (2006.01)
A61F 2/70 (2006.01)

(52) U.S. Cl.
CPC . A61F 2002/701 (2013.01); A61F 2002/7615 (2013.01); A61H 2230/60 (2013.01); A61H 2230/605 (2013.01)

(56) References Cited

U.S. PATENT DOCUMENTS

| | | | |
|---|---|---|---|
| 5,376,128 A | 12/1994 | Bozeman, Jr. | |
| 5,716,330 A * | 2/1998 | Goldman | A63B 21/00178 |
| | | | 482/51 |
| 6,344,062 B1 | 2/2002 | Abboudi et al. | |
| 2006/0015191 A1* | 1/2006 | Bergamasco | A61B 5/1071 |
| | | | 623/24 |
| 2008/0211302 A1 | 9/2008 | Hirota et al. | |
| 2008/0243265 A1 | 10/2008 | Lanier et al. | |
| 2010/0249675 A1 | 9/2010 | Fujimoto et al. | |
| 2012/0029399 A1* | 2/2012 | Sankai | A61B 5/04888 |
| | | | 601/40 |
| 2013/0041477 A1* | 2/2013 | Sikdar | A61B 8/085 |
| | | | 623/57 |

OTHER PUBLICATIONS

Patterson, Robert. A strain sensor controlled orthotic splint. Department of Physical MEdicine and Rehabilitation. Washington DC Nov. 15-19, 1970.*

Moromugi, Shunji. A sensor to measure the hardness of human tissue. IEEE Sensors. EXCO, Daegu, Korea. Oct. 22-25, 2006.*

Moromugi(1), Shunji. Muscle stiffness sensor to control an assistive device for the disabled. Artif Life Robotics. (2004) 8:42-45.*

Takahiko Mori,"Development of Power Assist System with Motion Estimation Using Model Predictive Control", IEICE Technical Report, Feb. 9, 2012, pp. 1-6, vol. 111, No. 432, Gifu, Japan.

Yukari Nakamura, International Search Report for PCT/JP2013/063004, May 27, 2013, Japanese Patent Office, WIPO, Geneva, Switzerland.

Dennler, Samuel, European Search Report for European Application 13806083, Apr. 29, 2015, European Patent Office, Munich, Germany.

* cited by examiner

ELECTRICALLY POWERED ARTIFICIAL HAND

TECHNICAL FIELD

The present invention relates to an electrically powered artificial hand, and more particularly to an electrically powered artificial hand that can be actively controlled based on an upper limb amputee's will of action.

BACKGROUND ART

Upper limb amputees use prostheses for restoring the shapes and the functions of part or all of the forearms or upper arms that have been lost by accidents, diseases, or other reasons. Known prostheses include a passive prosthesis for restoring the appearance of an upper limb, an active prosthesis (active artificial hand) for restoring functions of an upper limb for enabling various movements such as grasping objects by making a part corresponding to an elbow or a hand movable with the use of a movement of the shoulder joint or the shoulder blade, and a functional prosthesis with a plurality of attachments such as hooks attached replaceable for performing specific operations. Also known are a myoelectric prosthesis, which detects changes in the small current generated when muscles contract (surface myoelectric potential) and drives a built-in motor for restoring functions such as a grasping operation. Myoelectric prosthesis is sometimes classified as one type of active prostheses.

The active artificial hand uses a looped strap commonly called harness wound around a shoulder so that the movements of the shoulder joint or the like are transmitted to a terminal device at the distal end of the artificial hand by the tension of a plurality of wires (cables) to enable the terminal device to grasp an object. The terminal device may be formed by a pair of arms, for example, which are controlled to open and close by increasing or decreasing the distance between the arms so as to hold and grip (or sandwich) an object from two directions. Also known is a terminal device formed by three arms, with the two arms (corresponding to an index finger and a middle finger) and the one arm (corresponding to a thumb) opposite thereto being controlled to open and close for performing the operation of gripping an object more stably.

The myoelectric prosthesis, on the other hand, has a sensor that detects surface myoelectric potential, and electrically controls a terminal device in accordance with the amount of change in the surface myoelectric potential detected by the sensor. With the use of these active prosthesis or myoelectric prosthesis, an upper limb amputee, being able to control a terminal device by his/her own will of action, can perform basic movements in everyday life without the aid of a care giver and improve the quality of life.

However, these active prostheses and the like had the following problems. Namely, the active prostheses are driven by using a plurality of wires, so that they have been large because of the mechanisms for driving the harnesses and wires and heavier than passive prostheses. Because of this, some users have hesitated to use the prosthesis depending on where they have been because of the rugged outlook, or found it hard to carry the prosthesis around because of its heavy weight. Also, some users have required training for a certain period of time to master the operation of the active prostheses, because the terminal devices have been mechanically driven via the tension of the plurality of wires based on subtle movements of the shoulder joint or the like on which the harness have been wound around. Sometimes, depending on the posture of the upper limb amputee, for example, when the upper limb amputee has bent down, the wires have not been successfully transmitted movements of the shoulder joint, which has imposed limitations on the control of the active prosthesis.

Myoelectric prostheses, on the other hand, are electrically controlled based on very small surface myoelectric potentials, so that they have been able to be formed compactly as compared to the wire-driven type, and also have been able to reduce their weight. However, surface myoelectric potential has been hardly generated stably and being largely dependent on individuals. Commonly known problems have been that some users simply have not been able to control myoelectric prostheses at all, or the prostheses have been prone to unwanted operations because of the unreliable control reproducibility. Another problem has been that, despite the need of teaching by a professional trainer for mastering the operation of either the active prosthesis or the myoelectric prosthesis, sometimes sufficient trainings and teachings have not been available because of the shortage in the absolute number of such trainers.

SUMMARY OF THE INVENTION

Problems to be Solved by the Invention

In view of the circumstances described above, it is an object of the present invention to provide an electrically powered artificial hand that can be constructed with a simple configuration, the operation of which is easy to master and the control of which is highly reproducible.

Solutions to the Problems

To solve the problems described above, an electrically powered artificial hand of the present invention includes "a shape-detecting sensor attached to part of a forearm or an upper arm of an upper limb amputee for detecting a shape of the forearm or the upper arm, a hand section having at least a pair of arms that are capable of opening and closing movements, and a main control unit body electrically connected to the shape-detecting sensor and including a sensor signal-receiving circuit that receives a sensor signal output from the shape-detecting sensor in accordance with a shape of the forearm or the upper arm, and a control signal-generating and -sending circuit that generates a control signal based on the received sensor signal and sends the control signal to the electrically connected hand section so as to control opening and closing movements of the arms based on a control direction and a control magnitude contained in the control signal, the control direction for controlling a direction of movement of the arms being determined in accordance with a direction of a change in shape from a previously prescribed initial shape of the forearm or the upper arm, and the control magnitude for controlling a distance of movement of the arms being determined based on an amount of the change in shape from the initial shape."

The shape-detecting sensor here detects the shape of the forearm or the upper arm and outputs sensor signals that are sensor output potentials it generates. If the shape-detecting sensor is attached to the upper limb amputee who has lost part of the forearm below the elbow, for example, such as to be wound around the distal end of the remaining forearm, the shape of the forearm part can be detected based on the movements of the muscle tissues immediately under the skin of the forearm. The muscle conditions in such part hardly change because the user is unlikely to lose or gain weight drastically within a few days, so that it is relatively easy to control the direction and amount of the change in the shape. The upper limb amputee can thus change the shape of the forearm part or the like by moving the muscle tissues according to his/her will of action, and such a shape change can be detected by the shape-detecting sensor.

Examples of changes in the shape of the forearm to be detected may include an internal rotation movement in which the forearm is rotated inwardly around the elbow, and an external rotation movement in which the forearm is rotated outwardly. In this case, the shape of the forearm (change in the shape) between the internal rotation limit position where the forearm is rotated internally to the limit of the movable range and the external rotation limit position where the forearm is rotated externally to the limit of the movable range may be detected by the shape-detecting sensor. Instead of the internal/external rotation movements, shapes that change with the bending movement of bending the elbow or stretching movement of stretching the elbow may be detected by attaching the shape-detecting sensor near the elbow bone, or shapes that change with the raising and lowering movements of the arm around the shoulder joint may be detected by attaching the shape-detecting sensor near the shoulder joint. As the shape-detecting sensor, a strain sensor that detects a strain based on a change in the shape of the forearm or upper arm, or a potentiometer that rotates in accordance with a shape change, may be used. Using a strain sensor provides an advantage that a circuit for temperature compensation can be omitted, because the strain sensor will be kept at a constant temperature by the body temperature of the upper limb amputee.

The hand section may be one of the "terminal devices" mentioned above used as the distal end of a conventional myoelectric prosthesis, and may include, for example, at least a pair of arms, an arm pivot part pivotally supporting the arms such that arm ends can approach or separate from each other, and an opening/closing mechanism with a drive motor for causing the at least one pair of arms to open or close based on a received control signal.

The main control unit body, on the other hand, receives sensor signals output from the shape-detecting sensor, generates control signals based on the received signals, and sends the signals out, for opening and closing the arms of the hand section that are the control target (to be described later in detail). To be more specific, the control signal-generating and -sending circuit generates and sends out control signals determined based on the direction and amount of the change in shape from a previously prescribed initial shape of the forearm or upper arm. The control signals determine a control direction corresponding to the direction of the change in shape, and a control magnitude corresponding to the amount of the change in shape, for the opening and closing of the arms, whereby the hand section can be controlled in accordance with the shape change of the forearm or the upper arm. The direction of the change in shape from the initial shape may indicate the direction of rotation, either internally or externally, from the initial shape, for example, with the internal/external rotation movements described above. Therefore, if the amount of the change in shape of the forearm or upper arm is large, the control magnitude of arms becomes accordingly large, while, if the amount of the change in shape of the forearm or upper arm is small, the control magnitude of arms becomes accordingly small. The main control unit body may be configured, for example, with microcomputers such as PICs (Peripheral Interface Controllers), S8 microcomputers, or FPGAs (Field Programmable Gate Arrays), various switches, LEDs, and other parts.

Therefore, according to the electrically powered artificial hand of the present invention, the pair of arms of the hand section are moved to open and close by detecting a change in shape (direction or amount of a shape change) of the forearm or upper arm by a shape-detecting sensor, so that the artificial hand can be constructed with a simple configuration, as compared to wire-driven active prostheses. The shapes of the forearm or the upper arm are detected, i.e., changes in shape, in the internal/external rotation movements of the forearm around the elbow, or bending/stretching movements of the elbow, or raising/lowering movements of the arm around the shoulder joint, are detected. These movements are simple and the senses of these movements are easy to learn, so that it does not take a long time to master the operation as compared to generating surface myoelectric potential in a stable manner. Since the movements are simple, the direction or amount of the change in shape can readily be controlled, so that there is less possibility of unwanted operations, and thus high reproducibility of hand section movements is achieved reliably.

At least one pair of arms of the hand section can be controlled to open and close corresponding to the direction and amount of the change in shape of the forearm or upper arm based on the sensor signals from the shape-detecting sensor attached on the forearm or upper arm of the upper limb amputee. Thus, at least one pair of arms can sandwich objects or the like, so that the hand section can perform a gripping operation.

In addition to the configuration described above, the electrically powered artificial hand of the present invention may further include "a second shape-detecting sensor attached to a body part of the upper limb amputee at a different position from the position where the (first) shape-detecting sensor is attached for detecting a shape of the body part, wherein the main control unit body is electrically connected to the second shape-detecting sensor and further includes a second sensor signal-receiving circuit that receives a second sensor signal output from the second shape-detecting sensor in accordance with a shape of the body part, and wherein the control signal generated by the control signal-generating and -sending circuit based on the received second sensor signal includes a signal regarding a content of a movement of the arms determined based on a direction of a change in shape from a previously prescribed second initial shape of the body part, and a signal regarding an actual movement of the arms determined based on a second amount of the change in shape from the second initial shape."

Thus, according to the electrically powered artificial hand of the present invention, the second shape-detecting sensor is attached to a body part of the upper limb amputee at a different position from the position where the (first) shape-detecting sensor is attached, such as, a forearm, upper arm, shoulder, face, lower limbs and the like, and outputs the second sensor signal. This allows the main control unit body to generate a control signal based on the second sensor signal in accordance with a direction and a second amount of a change in shape from the previously prescribed second initial shape of the body part, in addition to the sensor signal for controlling the opening/closing movements of the arms. As a result, complex control of the hand section is made possible, in addition to the control operation for opening and closing the arms.

For example, the (first) shape-detecting sensor may be attached to the forearm and set so as to be able to control the opening/closing movements of the arms based on internal/external rotation movements of the forearm, while the second shape-detecting sensor may be attached to the elbow and set so as to be able to fix the arms at a given opening/closing position and to cancel the fixing movement (corresponding to types of arm movements) based on the bending/stretching movements of the elbow. More specifically, when the second initial shape is changed with the elbow being bent in a bending direction, the arms may be controlled to be fixed in an open/close position, while, when the shape is changed with the elbow being stretched in a stretching direction, the arms may be controlled to be released from the fixed state. The opening/closing movements of the arms are controlled such that the fixed state is achieved or canceled when the second amount of the change in shape from the second initial shape exceeds a previously prescribed value. This way, when an object is gripped with the arms, for example, it is not necessary to continuously perform an operation of controlling the arms to move in the closing direction all the time (e.g., internal rotation movement). Instead, the arms can be kept closed by performing the fixing operation achieved by the second shape-detecting sensor (e.g., elbow bending movement) once the arms are closed by the internal rotation movement. Another examples of control of the arms with the use of the second shape-detecting sensor include configuring the arms of the hand section to be controllable around multiple axes and rotating the arms around their axes in accordance with the bending/stretching movements of the elbow (which reproduces rotating movements of a human wrist), and bending and stretching all or part of the arms (which reproduces bending and stretching of a wrist or fingers). This way, complex movements of human hand/fingers are reproducible.

In addition to the configuration described above, the electrically powered artificial hand of the present invention may further include "an initial shape change-setting circuit that changes settings so that a given shape of the forearm or the upper arm is set as the initial shape, and/or a given shape of the body part is set as the second initial shape."

According to the electrically powered artificial hand of the present invention, with the initial shape change-setting circuit in the main control unit body, a previously prescribed initial shape of the forearm or the upper arm, or a previously prescribed second initial shape of the body part, can be changed to a given shape. In the case with internal/external movements of the forearm, for example, the shape of the forearm at the external rotation limit position, or the shape of the forearm when it is rotated externally to the limit of the movable range, is set as an initial shape by the initial shape change-setting circuit. This way, the forearm changes in shape in a greater amount in the internal rotation direction from the external rotation limit position to the internal rotation limit position than the amount of the change in shape from the one between the internal rotation limit position and the external rotation limit position set as the initial shape. Accordingly, the control magnitude in the controlled movement of the arms in accordance with such amount of the change in shape becomes large. This allows the movable ranges of arms to be extended and the control magnitude to be increased.

In addition to the configuration described above, the second shape-detecting sensor of the electrically powered artificial hand of the present invention may be attached to an acromion of the upper limb amputee.

Thus, according to the electrically powered artificial hand of the present invention, the acrominon of the upper limb amputee is the part where the second shape-detecting sensor is attached. Here, the acromion refers to an area around the part of the scapula, which protrudes horizontally outward from the upper end of the glenohumeral joint that articulates with the upper arm. At the inner side of the acromion is a plane acromioclavicular joint that articulates with the clavicle. Thus, the second shape-detecting sensor is attached on the acromion that is away from the (first) shape-detecting sensor attached on the forearm or the upper arm. Therefore, the shapes of the forearm or the upper arm and around the acromion detected by both sensors do not interfere with each other by their movements, so that the control stability of the hand section by these sensors is improved. The acromion is a part that can be moved voluntarily by the upper limb amputee relatively easily and whose shape change is readily distinguishable. Accordingly, control reproducibility of the electrically powered artificial hand is made stable.

Effects of the Invention

As described above, the present invention can provide an electrically powered artificial hand that can be constructed with a simple configuration, the operation of which is easy to master and the control of which is highly reproducible.

EMBODIMENTS OF THE INVENTION

Figure 1:
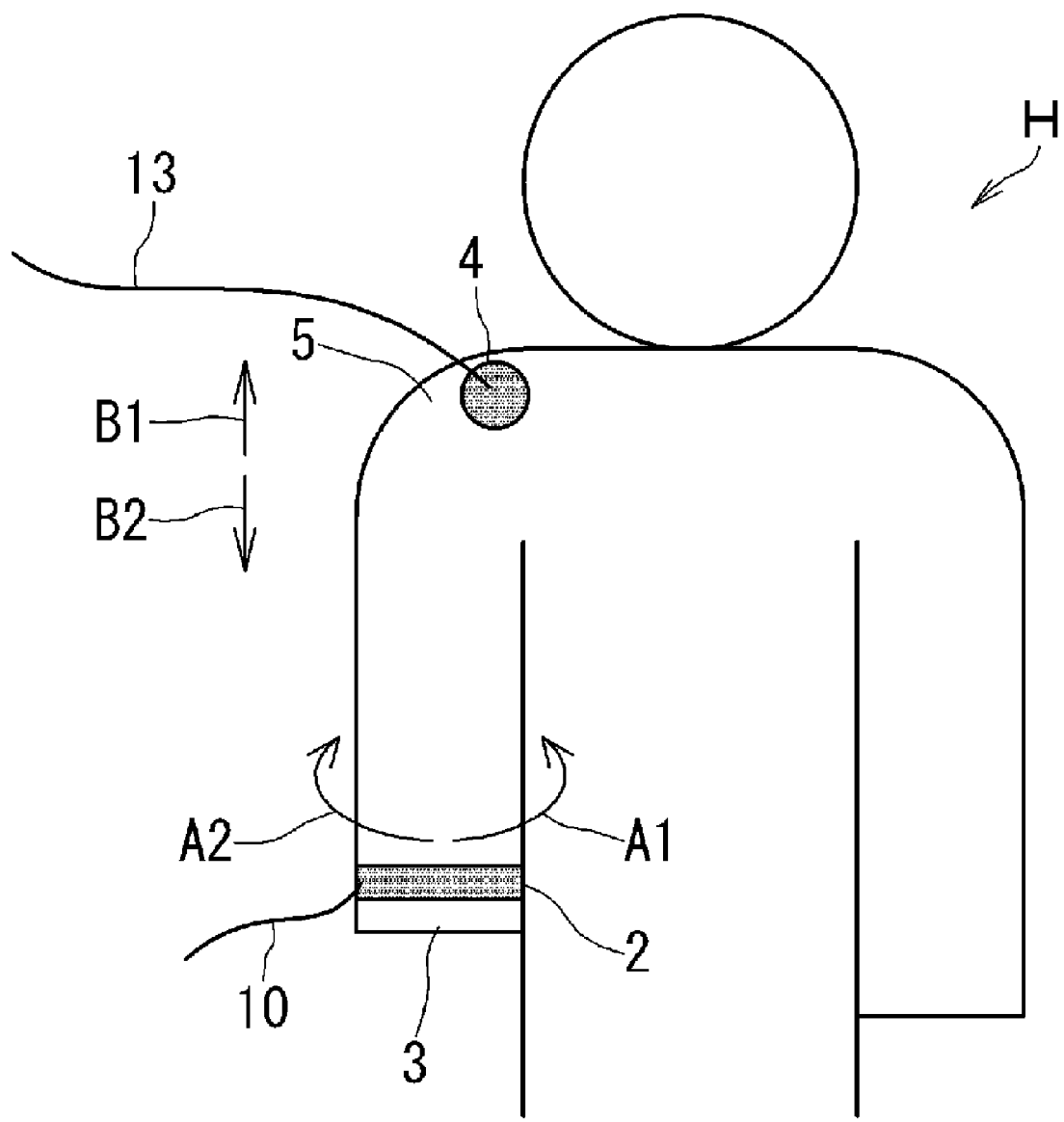
FIG. 1 is an explanatory diagram illustrating a condition of use of an electrically powered artificial hand of one embodiment.

Hereinafter, an electrically powered artificial hand 1 according to one embodiment of the present invention will be described with reference to FIG. 1 to FIG. 3. The electrically powered artificial hand 1 of this embodiment (which may also referred to herein as a "prosthesis") is illustrated as one that controls a hand section 6 thereof with a (first) shape-detecting sensor 2 attached to part of a forearm 3 of an upper limb amputee H for detecting the shape of the forearm 3 associated with an internal rotation movement A1 and an external rotation movement A2 (see arrows in FIG. 1) of the forearm 3, and a second shape-detecting sensor 4 attached to an acromion 5 (corresponding to a body part) for detecting the shape near the acromion 5 that changes with a shoulder elevation movement B1 and a shoulder depression movement B2 (see arrows in FIG. 1).

More specifically, the electrically powered artificial hand 1 of this embodiment is configured to control the pair of arms 7a and 7b (to be described in more detail later) of the hand section 6 to come close to each other so that they are "closed form" corresponding to a shape detected upon an internal rotation movement A1 of the forearm 3, and to control the pair of arms 7a and 7b to move away from each other so that they are "open form" corresponding to a shape detected upon an external rotation movement A2 of the forearm 3. The arms 7a and 7b may also be referred to herein as "levers"). Further, the artificial hand is configured to control the arms 7a and 7b to become fixed at a given open/close position in accordance with a shape near the acrominon 5 detected upon the shoulder joint including the acrominon 5 being raised, and to control the arms to be released from the fixed state in accordance with a shape near the acrominon 5 detected upon the shoulder joint including the acrominon 5 being lowered.

The electrically powered artificial hand 1 of this embodiment includes the (first) shape-detecting sensor 2 attached to the forearm 3 of the upper limb amputee H, the second shape-detecting sensor 4 attached to the acromion 5 of the upper limb amputee H, a main control unit body 8 electrically connected to each of the shape-detecting sensor 2 and the second shape-detecting sensor 4, and the hand section 6 connected to the main control unit body 8. The hand section 6 may be attached to the forearm 3 of the upper limb amputee H.

The shape-detecting sensor 2 is made of a sensor portion 2a and a thin plate-like (strip-like) metal plate 9 on which the sensor portion 2a is bonded. This metal plate 9 is wound around the forearm 3 (see FIG. 1), with the sensor portion 2a side in contact with the forearm 3. Attachment of the shape-detecting sensor 2 is thus complete. To keep the attached state of the metal plate 9 wound around the forearm 3, the metal plate 9 is wrapped with a strip-like attachment band (not shown) that has surface fasteners at one end and at the other.

For the electrically powered artificial hand 1 of this embodiment, a thin flat plate-like strain sensor is used as the shape-detecting sensor 2. With this shape-detecting sensor 2 attached on the forearm 3, the strain sensor deforms in conformity with the shape of the forearm 3 that changes with an internal rotation movement A1 or external rotation movement A2, and outputs sensor signals 14 in accordance with the direction, amount and the like of the change in shape. The shape-detecting sensor 2 is electrically connected to the main control unit body 8 via a connection cord 10 extending from the sensor portion 2a. With the use of the strain sensor, a drop in detection accuracy of the strain amount due to a temperature change is unlikely to occur, because the strain sensor is substantially at the same temperature as the body temperature of the upper limb amputee H.

On the other hand, the second shape-detecting sensor 4 includes a base body 11, a sensor portion 4a mounted near the center on one side of the base body 11, and a generally circular adhesive portion 12 provided around the sensor portion 4a. With the stickiness of the adhesive portion 12 around the sensor portion 4a, the second shape-detecting sensor 4 can be affixed to make contact with part of the acromion 5. This way, the second shape-detecting sensor 4 with a novel configuration can be attached to the upper limb amputee H in addition to the (first) shape-detecting sensor 2. In addition, a second shape-detecting sensor 4 that has the same configuration as that of the (first) shape-detecting sensor 2 may be used. The second shape-detecting sensor 4 is further electrically connected to the main control unit body 8 via a connection cord 13 extending from the sensor portion 4a.

The main control unit body 8 is formed by a control board (not shown) including a control circuit that is configured with FPGAs, various switches, LEDs, and the like mentioned above for controlling the hand section 6. The main control unit body 8, as its functional configuration, includes, as shown in FIG. 3, a (first) sensor signal-receiving circuit 15 that receives sensor signals 14 output from the shape-detecting sensor 2 via the connection cord 10, a second sensor signal-receiving circuit 17 that receives second sensor signals 16 output from the second shape-detecting sensor 4 via the connection cord 13, and a control signal-generating and -sending circuit 19 that generates control signals 18 for controlling the hand section 6 based on the received sensor signals 14 and second sensor signals 16 and sends the signals to the hand section 6. The control signal-generating and -sending circuit 19 can generate control signals 18 that determine a control direction, control magnitude, and control speed respectively corresponding to a direction, amount, and speed of a change in shape from a previously prescribed initial shape (to be described later in more detail) of the forearm 3 based on the received sensor signals 14, and can generate control signals 18 determined corresponding to a direction and a second amount of a change in shape from a previously prescribed second initial shape (to be described later in more detail) of the acromion 5 based on the received second sensor signals 16.

The main control unit body 8, as its functional configuration, further includes, a reference shape-setting circuit 20 for presetting a shape of the forearm 3 associated with an internal rotation movement A1 and a shape of the forearm 3 associated with an external rotation movement A2, with the shape-detecting sensor 2 attached on the forearm at the start of operation of the electrically powered artificial hand 1, as well as a shape near the acromion 5 associated with a shoulder elevation movement B1 and a shape near the acromion 5 associated with a shoulder depression movement B2, with the second shape-detecting sensor 4 attached on the acromion 5, each as a reference shape, and an initial shape change-setting circuit 21 that changes settings so that a given shape of the forearm 3 or a shape near the acromion 5 detected respectively by the (first) shape-detecting sensor 2 or the second shape-detecting sensor 4 is set as the (first) initial shape or the second initial shape.

The reference shape-setting circuit 20 has sensor signals 14 stored in advance that correspond to reference shapes of the forearm 3 with which an internal rotation movement A1 and an external rotation movement A2 were carried out to the limits of respective movable ranges (internal rotation limit position and external rotation limit position) at the start of operation, as well as second sensor signals 16 stored in advance that correspond to reference shapes of the acromion with which a shoulder elevation movement B1 and a shoulder depression movement B2 were carried out to the limits of respective movable ranges (shoulder elevation limit position and shoulder depression limit position). This way, the shapes at respective upper limits and lower limits of the internal rotation movement A1, external rotation movement A2, shoulder elevation movement B1, and shoulder depression movement B2 are preset as reference shapes. A reference shape setting button 27 connected to the reference shape-setting circuit 20 is provided to the main control unit body 8 for setting reference shapes, to detect sensor signals 14 and second sensor signals 16 corresponding to respective reference shapes. The "previously prescribed initial shape" of the forearm 3 at the start of operation is an intermediate shape corresponding to an average value of sensor signals 14 at the internal rotation limit position and the external rotation limit position set as described above. The "previously prescribed second initial shape" of the acromion 5 at the start of operation is an intermediate shape corresponding to an average value of second sensor signals 16 at the shoulder elevation limit position and the shoulder depression limit position.

The initial shape change-setting circuit 21, on the other hand, changes the settings so that a given shape of the forearm 3 or near the acromion 5 respectively detected by the (first) shape-detecting sensor 2 or the second shape-detecting sensor 4 is registered as an initial shape or a second initial shape. This enables the movable ranges of the arms 7*a* and 7*b* to be extended. The main control unit body 8 additionally includes other elements such as a power supply circuit or the like (not shown) to perform the functions of configurations described above. Similarly to the reference shape setting button 27, an initial shape setting button 28 connected to the initial shape change-setting circuit 21 is provided to the main control unit body 8. In addition, the main control unit body 8 includes a temporary storage circuit 26 for temporarily storing sensor signals 14 and second sensor signals 16 corresponding to preset reference shapes, prescribed initial shape and second initial shape, and changed initial shape and second initial shape changed by the initial shape change-setting circuit 21.

The hand section 6 includes the pair of arms 7*a* and 7*b*, an arm pivot part 22 pivotally supporting respective arm ends on one side such as to be rotatable relative to each other so as to perform approaching (closing) and separating (opening) movements of both arm ends on the other side, a drive motor 23 that generates a drive force for opening and closing the arms 7*a* and 7*b*, and an opening/closing mechanism 25 for opening and closing the arms 7*a* and 7*b* based on control signals 18 sent from the main control unit body 8 and received via the main control unit body 8 and a connection cord 24. Similarly to the main control unit body 8, other configurations such as a power supply circuit or the like for supplying power to the drive motor 23 are not shown.

Next, one example of use of the electrically powered artificial hand 1 of this embodiment will be described. As a precondition of use, the shape-detecting sensor 2 and second shape-detecting sensor 4 are attached on the forearm 3 and acromion 5, respectively, of the upper limb amputee H. The respective power supply circuits of the main control unit body 8 and hand section 6 are in operation. Thus, sensor signals 14 relating to the shape of the forearm 3, and second sensor signals 16 relating to the shape near the acromion 5, are continuously output from the shape-detecting sensor 2 and second shape-detecting sensor 4, respectively.

In this state, first, reference shapes of the forearm 3 and around the acromion 5 are set by the reference shape-setting circuit 20. First, the upper limb amputee H performs an internal rotation movement A1 by his/her own will of action in which the forearm 3 is internally rotated to a limit of the movable range. This internal rotation movement A1 changes the shape of the forearm 3, and a sensor signal 14 relating to the shape of the forearm 3 at the internal rotation limit position is output from the shape-detecting sensor 2. The reference shape-setting circuit 20 in the main control unit body 8 receives this sensor signal 14 via the sensor signal-receiving circuit 15 and stores it as data that specify a reference shape at the internal rotation limit position in the temporary storage circuit 26. The sensor signal 14 is stored in the temporary storage circuit 26 when the reference shape-setting button 27 provided to the main control unit body 8 is depressed. Next, the upper limb amputee H performs an external rotation movement A2 by his/her own will of action in which the forearm 3 is externally rotated to a limit of the movable range. This external rotation movement A2 changes the shape of the forearm 3, and a sensor signal 14 relating to the shape of the forearm 3 at the external rotation limit position is output from the shape-detecting sensor 2. This sensor signal 14 is stored in the temporary storage circuit 26 as data that specify a reference shape at the external rotation limit position in the temporary storage circuit 26 when the reference shape-setting button 27 mentioned above is depressed. As a result, two sensor signals 14 are stored, each corresponding to the shape of the forearm 3 at the internal rotation limit position in the internal rotation movement A1, and the shape of the forearm 3 at the external rotation limit position in the external rotation movement A2 (reference shapes). From these two stored sensor signals 14, a sensor signal 14 is determined that relates to the movable range of the forearm 3 and an initial shape that corresponds to an intermediate shape between the two reference shapes. Similarly, second sensor signals 16 output from the second shape-detecting sensor 4 respectively relating to the shoulder elevation movement B1 and shoulder depression movement B2 are stored in the temporary storage circuit 26 via the second sensor signal-receiving circuit 17 as data that specify reference shapes at upper and lower limit positions of the shoulder. Thus second sensor signals 16 are determined, each relating to the reference shapes at the upper and lower limit positions in the shoulder movements, and a second initial shape that corresponds to an intermediate shape between the two reference shapes.

After these reference shapes, initial shape, and second initial shape are set, the hand section 6 is controlled based on the outputs from the (first) shape-detecting sensor 2 and second shape-detecting sensor 4. As described above, sensor signals 14 relating to the shape of the forearm 3, and second sensor signals 16 relating to the shape near the acromion 5, are continuously output from the shape-detecting sensor 2 and second shape-detecting sensor 4, respectively. The main control unit body 8 receives the sensor signals 14 output from the shape-detecting sensor 2 via the sensor signal-receiving circuit 15, and receives the second sensor signals 16 output from the second shape-detecting sensor 4 via the second sensor signal-receiving circuit 17. The control unit then generates control signals 18 based on the received sensor signals 14 and second sensor signals 16. The control signals 18 are generated by determining a control magnitude of the arms 7*a* and 7*b* (also referred to herein as a control amount of displacement) corresponding to the degree of the change in shape. To do so, a control direction (opening or closing direction) of the arms 7*a* and 7*b* is first determined from a direction of a change in shape (internal or external) that is determined based on the sensor signal 14 being received and the sensor signals 14 respectively relating to the reference shapes at the internal rotation limit position and the external rotation limit position, and the initial shape, stored in the temporary storage circuit 26, and, the amount of change in the shape of the forearm 3 is determined from a deviation between the sensor signal 14 being received and the sensor signal 14 relating to the initial shape. A control speed of opening and closing movements of the arms 7*a* and 7*b* is also calculated from a speed of change based on the magnitude of the rate of change of the sensor signals 14 continuously output from the shape-detecting sensor 2 per a predetermined time. Thus control signals 18 relating to the control operation that determine the control magnitude and control speed of the opening and closing movements of the arms 7*a* and 7*b* are generated. After that, the generated control signals 18 are sent from the main control unit body 8 to the hand section 6. According to the setting in this embodiment, the arms 7*a* and 7*b* of the hand section 6 are controlled to close if the sensor signal 14 is based on an internal rotation movement A1, whereby the arms 7*a* and 7*b* are fully closed at the internal rotation limit position, whereas the arms 7*a* and 7*b* are controlled to open if the sensor signal 14 is based on an external rotation movement A2, whereby the arms 7*a* and 7*b* are fully opened at the external rotation limit position.

The opening/closing mechanism 25 of the hand section 6 receives the sent-out control signals 18 and drives the drive motor 23 in accordance with the control direction, control magnitude, and control speed included in the control signals 18. The pair of arms 7a and 7b can be opened and closed this way. As a result, a gripping movement of gripping an object between the arms 7a and 7b, and a movement that releases the grip can be performed.

Further, the electrically powered artificial hand 1 of this embodiment is capable of controlling the hand section 6 with the use of the second shape-detecting sensor 4 attached on the acromion 5 in combination with the control in accordance with the shape change of the forearm 3 described above. The shape-detecting sensor 2 continuously outputs sensor signals 14 as mentioned above. Therefore, even if the arms 7a and 7b are controlled to close by the control signal 18, the upper limb amputee H may need to continue the internal rotation movement A1 of the forearm 3 all the time to keep this state, forcing the forearm 3 to be in a tense state for a long time. With this in view, the electrically powered artificial hand 1 of this embodiment allows the arms 7a and 7b to become fixed at a given open/close position, or to be released from such a fixed state, with the use of the second shape-detecting sensor 4.

Namely, after the control of the arms 7a and 7b to grip an object has been executed with the forearm 3 and the (first) shape-detecting sensor 2, a second sensor signal 16 is output from the second shape-detecting sensor 4 relating to the shape around the acromion 5 at an upper limit position of the shoulder, through a shoulder elevation movement B1 by the upper limb amputee H. This causes the control signal-generating and -sending circuit 19 to generate a control signal 18 to fix the arms 7a and 7b at an open/close position, which is then sent to the hand section 6. The control signal 18 is generated by determining a direction of a change in shape (shoulder elevation or depression) based on the second sensor signal 16 being received and the second sensor signals 16 respectively relating to the reference shapes at the upper and lower limit positions of the shoulder, and the second initial shape, stored in the temporary storage circuit 26. It is then determined whether the arms 7a and 7b are to be fixed or released from a fixed state (corresponding to the content of the arm movement). A second amount of the change in shape around the acromion 5 is determined from a deviation between the sensor signal 16 being received and the sensor signal 16 relating to the second initial shape. The second shape-detecting sensor 4 of the electrically powered artificial hand 1 of this embodiment is provided for executing control to fix the arms 7a and 7b in an open or closed state, or to release them from a fixed state. Therefore, the control unit is configured to generate the control signal 18 for fixing the arms 7a and 7b or releasing them from a fixed state if a second amount of the change in shape obtained from the deviation mentioned above exceeds a previously prescribed value. The control signal 18 that contains a signal regarding an actual movement of the arms 7a and 7b for fixing the arms at an open/close position is thus generated and sent to the hand section 6. As a result, even though sensor signals 14 are output from the shape-detecting sensor 2 thereafter, the control of the hand section 6 based on these sensor signals 14 is canceled. Accordingly, the upper limb amputee H can move the forearm 3 freely. On the other hand, when the upper limb amputee H performs a shoulder depression movement B2, a second sensor signal 16 corresponding to the movement is output, and a control signal 18 that will cancel the fixed state is sent out.

The initial shape change-setting circuit 21 allows the settings to be changed so that a given shape of the forearm 3 or around the acromion 5 respectively detected by the (first) shape-detecting sensor 2 and the second shape-detecting sensor 4 are set as an initial shape or a second initial shape. For example, with the electrically powered artificial hand 1 of this embodiment, the forearm 3 is rotated externally to a limit of the movable range (external rotation limit position). The sensor signal 14 relating to the shape of the forearm 3 in such a state is stored in the temporary storage circuit 26 by depressing the initial shape-setting button 28 provided to the main control unit body 8. Thereby, the initial shape of the forearm 3 is set to be the one at the external rotation limit position. As a result, the amount of the change in shape in the internal rotation movement of the forearm 3 when rotated internally from the external rotation limit position becomes larger than the amount of the change in shape from the initial shape that was originally set based on the two reference shapes (at the internal rotation limit position and the external rotation limit position). Accordingly, the control magnitude of the opening and closing movements of the arms 7a and 7b determined corresponding to this amount of the change in shape becomes larger, so that the movable range of the forearm 3 is extended and the control magnitude of the arms 7a and 7b is increased.

As described above, the electrically powered artificial hand 1 of this embodiment can control the opening and closing of the arms 7a and 7b in accordance with a change in shape of the forearm 3 of the upper limb amputee H. Such a change in shape can be relatively easily brought about by the will of action of the upper limb amputee H, so that the operation stability (control reproducibility) can be made higher as compared to conventional wire-driven active prostheses or myoelectric prostheses based on surface myoelectric potentials. Therefore, the user can control the movements of the hand section 6 only after simple operation training. Accordingly, the time required for the training for the user to master the operation is made shorter as compared to conventional active prostheses.

Since the initial setting can be changed to a value obtained at a given position, the movable range can be extended easily. Mechanical configurations such as wires, harnesses and the like are largely omitted, so that the electrically powered artificial hand 1 itself can be produced in a compact and lightweight form. Limitations on conditions of use or difficulties in transportation can also be resolved. Myoelectric prostheses can be expensive to acquire (e.g., about 1,200,000 yen without an insurance coverage), since the application of insurance for users is strictly limited under the current law. Compared to the myoelectric prostheses that are not being widely available because of legal and economical restrictions, the artificial hand according to the present invention can be constructed with a simple configuration, and a reduction in the production cost can be expected.

While preferred embodiments of the present invention have been described above, the present invention is not limited to these embodiments and various improvements and design changes may be carried out as shown below without departing from the scope of the subject matter of the present invention.

Figure 2:
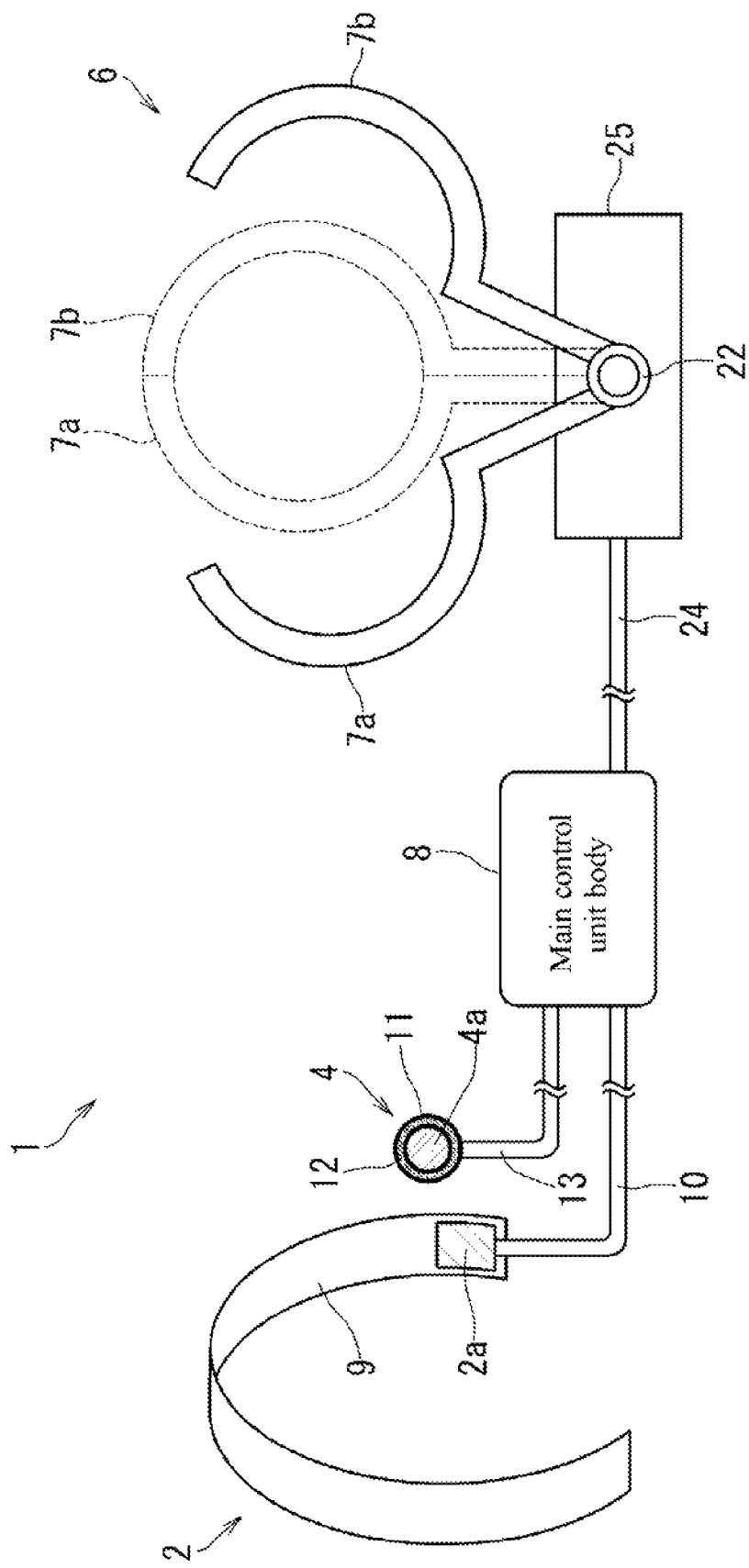
FIG. 2 is a schematic diagram illustrating a general configuration of the electrically powered artificial hand of this embodiment.
Figure 3:
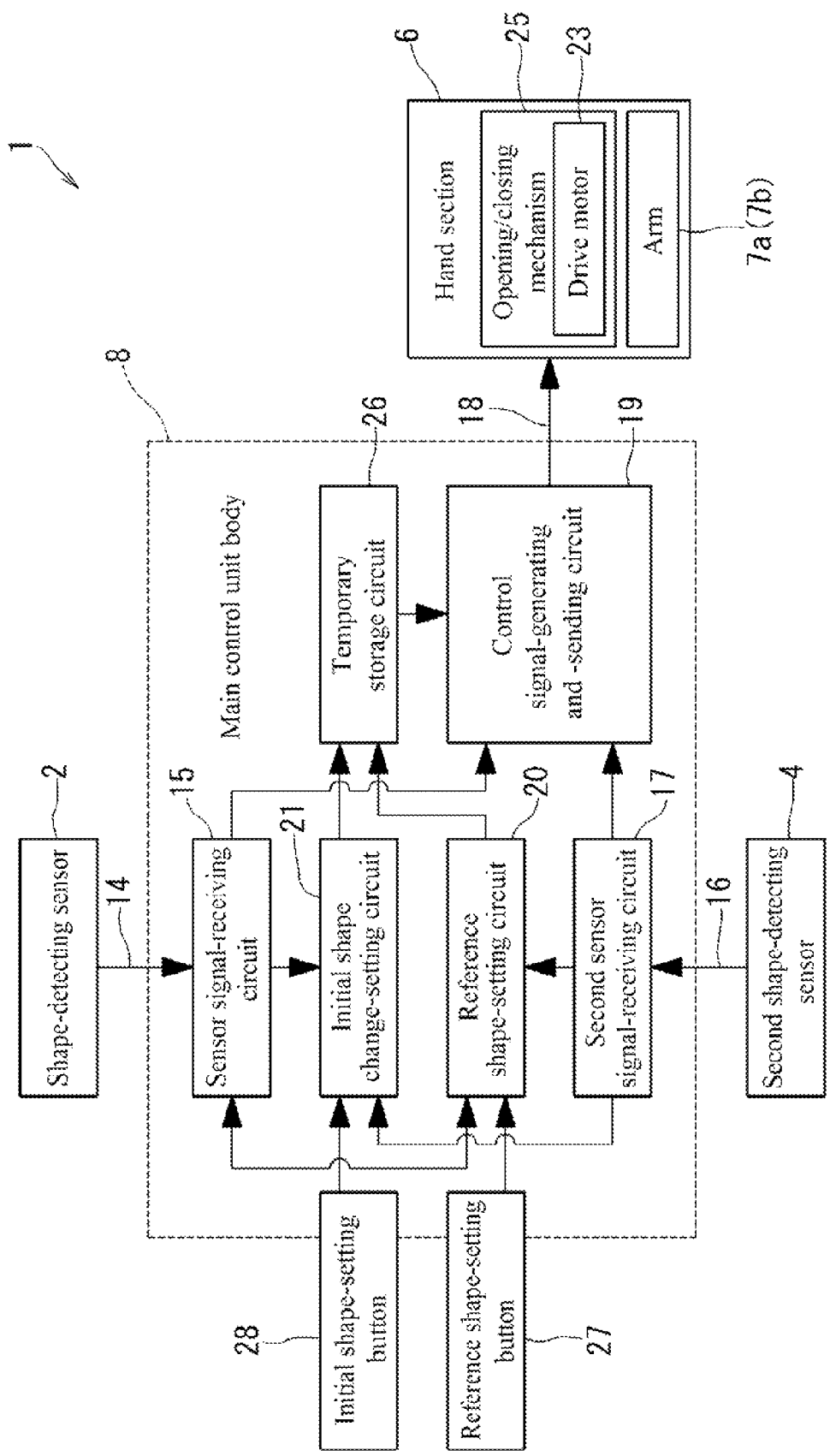
FIG. 3 is a block diagram illustrating the general configuration of the electrically powered artificial hand.

For example, the configuration of the hand section 6, which is schematically shown in FIG. 2, is not limited to this, and the hand section 6 may be controlled in a state attached to the forearm 3 of the upper limb amputee H. While the control described above is based on the internal rotation movement A1 and external rotation movement A2 of the forearm 3, the invention is not limited to this. The shape-detecting sensor 2 may be attached to the elbow of the upper limb amputee H to detect a shape associated with a bending movement and a stretching movement of the elbow. Also, while the second shape-detecting sensor 4 is attached to the acromion 5, the invention is not limited to this, and may be attached to the elbow, or, any other part that can freely be changed in shape voluntarily by the upper limb amputee H.

While the electrically powered artificial hand 1 of the embodiment described above uses strain sensors as the (first) shape-detecting sensor 2 and second shape-detecting sensor 4, the invention is not limited to this, and other sensors that can detect a shape change such as a potentiometer or the like may be used.

The invention claimed is:

1. An electrically powered prosthesis comprising: a first shape-detecting sensor configured to be attached to part of a forearm or an upper arm of an upper limb amputee and to detect a shape of said forearm or said upper arm and generate a sensor signal output, wherein the first shape-detecting sensor is a strain sensor; a hand section having at least a pair of levers that are capable of opening and closing movements; and a main control unit body electrically connected to said first shape-detecting sensor, said main control unit body including: a sensor signal-receiving circuit that receives the sensor signal output from said first shape-detecting sensor in accordance with a shape of said forearm or said upper arm, and a control signal-generating and -sending circuit that generates a control signal responsive to both direction and displacement information contained in said received sensor signal and sends said control signal to said electrically connected hand section so as to control opening and closing movements of said levers based on a control direction and a control amount of displacement contained in said control signal, the control direction for controlling a direction of movement of said levers being determined in accordance with a direction of a change in shape from a previously prescribed first initial shape of said forearm or said upper arm, and the control amount of displacement for controlling a distance of movement of said levers being determined based on an amount of the change in shape from the first initial shape.

2. The electrically powered prosthesis according to claim 1, wherein said first shape-detecting sensor detects a shape of said forearm that changes with an internal rotation movement in which said forearm is rotated inwardly around an elbow and with an external rotation movement in which the forearm is rotated outwardly.

3. The electrically powered prosthesis according to claim 1, further comprising a second shape-detecting sensor configured to be attached to a body part of said upper limb amputee at a different position from the position where said first shape-detecting sensor is configured to be attached, for detecting a shape of said body part and generate a second sensor signal output;

wherein said main control unit body is electrically connected to said second shape-detecting sensor and further includes a second sensor signal-receiving circuit that receives the second sensor signal output from said second shape-detecting sensor in accordance with a shape of said body part, and wherein said control signal generated by said control signal-generating and -sending circuit based on said received second sensor signal includes a signal regarding a content of a movement of said levers determined based on a direction of a change in shape from a previously prescribed second initial shape of said body part, and a signal regarding an actual movement of said levers determined based on a second amount of the change in shape from said second initial shape.

4. The electrically powered prosthesis according to claim 3, wherein said main control unit body further includes an initial shape change-setting circuit that changes settings so that a given shape of said forearm or said upper arm is set as said first initial shape, and a given shape of said body part is set as said second initial shape.

5. The electrically powered prosthesis according to claim 3, wherein said second shape-detecting sensor is configured to be attached to an acromion of said upper limb amputee.

6. A method for controlling the electrically powered prosthesis of claim 1, the method comprising the steps of:

Detecting the shape of said forearm or said upper arm with the first shape-detecting sensor and generating said signal output;

receiving the sensor signal output with the sensor signal-receiving circuit from said shape-detecting sensor in accordance with the shape of said forearm or said upper arm;

generating said control signal with the control signal-generating and sending circuit based on said received sensor signal, said control signal including a control direction for controlling the direction of movement of said levers and a control speed for controlling the speed of said levers, the control direction being determined in accordance with the direction of the change in shape from a previously prescribed initial shape of said forearm or said upper arm, the control speed being determined based on the speed of the change in shape from the initial shape; and sending said control signal to said electrically connected hand section.

* * * * *